(12) United States Patent
Berinato

(10) Patent No.: US 7,204,246 B1
(45) Date of Patent: Apr. 17, 2007

(54) AIR SELF-CONTAINED OXYGEN INHALER

(76) Inventor: Joseph Berinato, 6 Ave. B #3B, New York, NY (US) 10009

( * ) Notice: Subject to any disclaimer, the term of this patent is extended or adjusted under 35 U.S.C. 154(b) by 0 days.

(21) Appl. No.: 10/885,917

(22) Filed: Jul. 8, 2004

(51) Int. Cl.
*A61M 11/00* (2006.01)
*A61M 15/08* (2006.01)

(52) U.S. Cl. ............................ 128/200.14; 128/207.18

(58) Field of Classification Search ........... 128/200.14, 128/200.22, 200.23, 203.12, 203.22, 203.23, 128/207.18, 204.12, 205.21, 203.15, 205.22
See application file for complete search history.

(56) References Cited

U.S. PATENT DOCUMENTS

| | | | |
|---|---|---|---|
| 2,860,634 A * | 11/1958 | Duncan et al. ........ | 128/205.24 |
| 3,045,671 A * | 7/1962 | Updegraff .............. | 128/205.21 |
| 3,776,227 A * | 12/1973 | Pitesky et al. ......... | 128/205.21 |
| 3,809,084 A | 5/1974 | Hansen | |
| 4,671,270 A | 6/1987 | Kato | |
| 5,437,267 A * | 8/1995 | Weinstein et al. ..... | 128/200.23 |
| 5,750,077 A | 5/1998 | Schoen | |
| 5,901,703 A * | 5/1999 | Ohki et al. ............. | 128/203.12 |
| 6,505,622 B2 * | 1/2003 | Py ........................ | 128/203.18 |
| 2004/0112378 A1* | 6/2004 | Djupesland ............ | 128/203.12 |
| 2005/0045181 A1* | 3/2005 | Philipps et al. ........ | 128/207.18 |
| 2005/0072430 A1* | 4/2005 | Djupesland ............ | 128/206.11 |

* cited by examiner

*Primary Examiner*—Teena Mitchell

(57) ABSTRACT

A health apparatus for use by individuals. The apparatus is an oxygen inhaler that works in a manner analogous to that of a breath spray and an asthma inhaler. Rather than dispensing asthma medicine, however, the oxygen inhaler disperses a small volume of oxygen through the nose that would be available for inhalation by a user. The present invention could be used for both health reasons and for recreational use.

4 Claims, 3 Drawing Sheets

AIR SELF-CONTAINED OXYGEN INHALER

I. BACKGROUND OF THE INVENTION

The present invention concerns that of a new and improved health apparatus for use by individuals.

II. DESCRIPTION OF THE PRIOR ART

U.S. Pat. No. 5,750,077, issued to Schoen, discloses a battery-powered portable oxygen supply system using an endothermic reaction to produce pure oxygen for a user.

U.S. Pat. No. 4,671,270, issued to Kato, discloses a portable oxygen inhaler device comprised of a chlorate candle and a mask for assisting someone with difficulty breathing.

U.S. Pat. No. 3,809,084, issued to Hansen, discloses a portable dispenser capable of using air or compressed oxygen suited to cooperate with a body cavity, such as the mouth or nose, to carry dose of medicine.

III. SUMMARY OF THE INVENTION

The present invention concerns that of a new and improved health apparatus for use by individuals. The apparatus would be an oxygen inhaler that would work in a manner analogous to that of a breath spray and an asthma inhaler. Rather than dispensing asthma medicine, however, the oxygen inhaler would disperse a small volume of oxygen through the nose that would be available for inhalation by a user. The present invention could be used for both health reasons and for recreational use.

There has thus been outlined, rather broadly, the more important features of an oxygen inhaler that the detailed description thereof that follows may be better understood and in order that the present contribution to the art may be better appreciated. There are, of course, additional features of the oxygen inhaler that will be described hereinafter and which will form the subject matter of the claims appended hereto.

In this respect, before explaining at least one embodiment of the oxygen inhaler in detail, it is to be understood that the oxygen inhaler is not limited in its application to the details of construction and to the arrangements of the components set forth in the following description or illustrated in the drawings. The oxygen inhaler is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present oxygen inhaler. It is important, therefore, that the claims be regarded as including such equivalent constructions insofar as they do not depart from the spirit and scope of the present invention.

It is therefore an object of the present invention to provide an oxygen inhaler which has all of the advantages of the prior art and none of the disadvantages.

It is another object of the present invention to provide an oxygen inhaler which may be easily and efficiently manufactured and marketed.

It is another object of the present invention to provide an oxygen inhaler which is of durable and reliable construction.

It is yet another object of the present invention to provide an oxygen inhaler which is economically affordable and available for relevant market segment of the purchasing public.

Other objects, features and advantages of the present invention will become more readily apparent from the following detailed description of the preferred embodiment when considered with the attached drawings and appended claims.

IV. BRIEF DESCRIPTION OF THE DRAWINGS

V. DESCRIPTION OF THE PREFERRED EMBODIMENT

Figure 1:
FIG. 1 shows a perspective view of the present invention.
Figure 2:
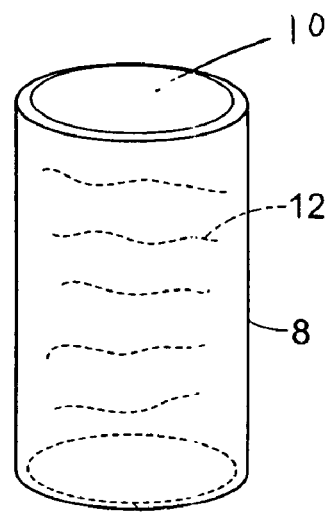
FIG. 2 shows a side view of an oxygen canister that would be used with the present invention.

FIG. 1 shows a perspective view of the present invention, while FIG. 2 shows a side view of an oxygen canister 8 that would be used with the present invention. Inhaler 2 would serve as a health apparatus for those would need additional oxygen, and in addition, inhaler 2 could also be used by healthy individuals in various situations to boost their energy and/or health.

Inhaler 2 would be shaped like a miniature shaving foam canister and would be operated in the same manner, but controlled by a sliding lever instead of a push-down button. Inhaler 2 has an outer casing 3 that has two ends, a top end and a bottom end, with the bottom end being open. To the top end of the inhaler 2 is attached a slide lever dispenser 4.

The oxygen canister 8 has two ends, a top end and a bottom end, and has a pressure valve 10 attached to the top end of the oxygen canister. Within the oxygen canister 8 is located a small amount of pressurized oxygen 12. The inhaler also has a nostril piece 6 would be made of soft rubber and tilt to fit comfortably under and against the user's nostrils. Nostril piece 6 has two ends, a first end and a second end, with the first end of the nostril piece 6 being attached to the top end of the outer casing.

Two tunnels 20 and 22 are located within the nostril piece 6, with each tunnel having two ends, a first end and a second end. The first end of each tunnel is located at the first end of the nostril piece 6, while the second end of each tunnel is located at the second end of the nostril piece 6.

The oxygen canister 8 would be connected to the outer casing 3 by inserting the top end of the oxygen canister 8 through the bottom end of the outer casing 3 until the pressure valve 10 of the oxygen canister 8 rested against the slide lever dispenser 4. If an individual wanted to utilize the inhaler 2, the user merely needs to activate the slide lever dispenser 4, which then temporarily engages with the pressure valve 10. This causes a small amount of oxygen 12 to be expelled out of the pressure valve 10 each time the dispenser lever 4 would be pushed downward, thereby causing the pressure valve 10 to become activated.

Oxygen expelled from the canister 8 would pass through the tunnels 20 and 22 within the nostril piece 6 and would be expelled through the second end of the tunnels 20 and 22 of the nostril piece 6. A person would ideally rest their nose on top of the cushioned nostril piece 6 in advance or would place their nose in the immediate vicinity of nostril piece 6 in advance of pushing down on dispenser lever 4.

This invention is not created solely for people in need of additional oxygen but also serves as a good measure to promote better health. It would increase awareness in the importance of breathing better air quality and could possibly be used as a good weapon in the fight against smoking.

Figure 3:
FIG. 3 shows a representative view of the present invention as it would appear in use.
Figure 4:
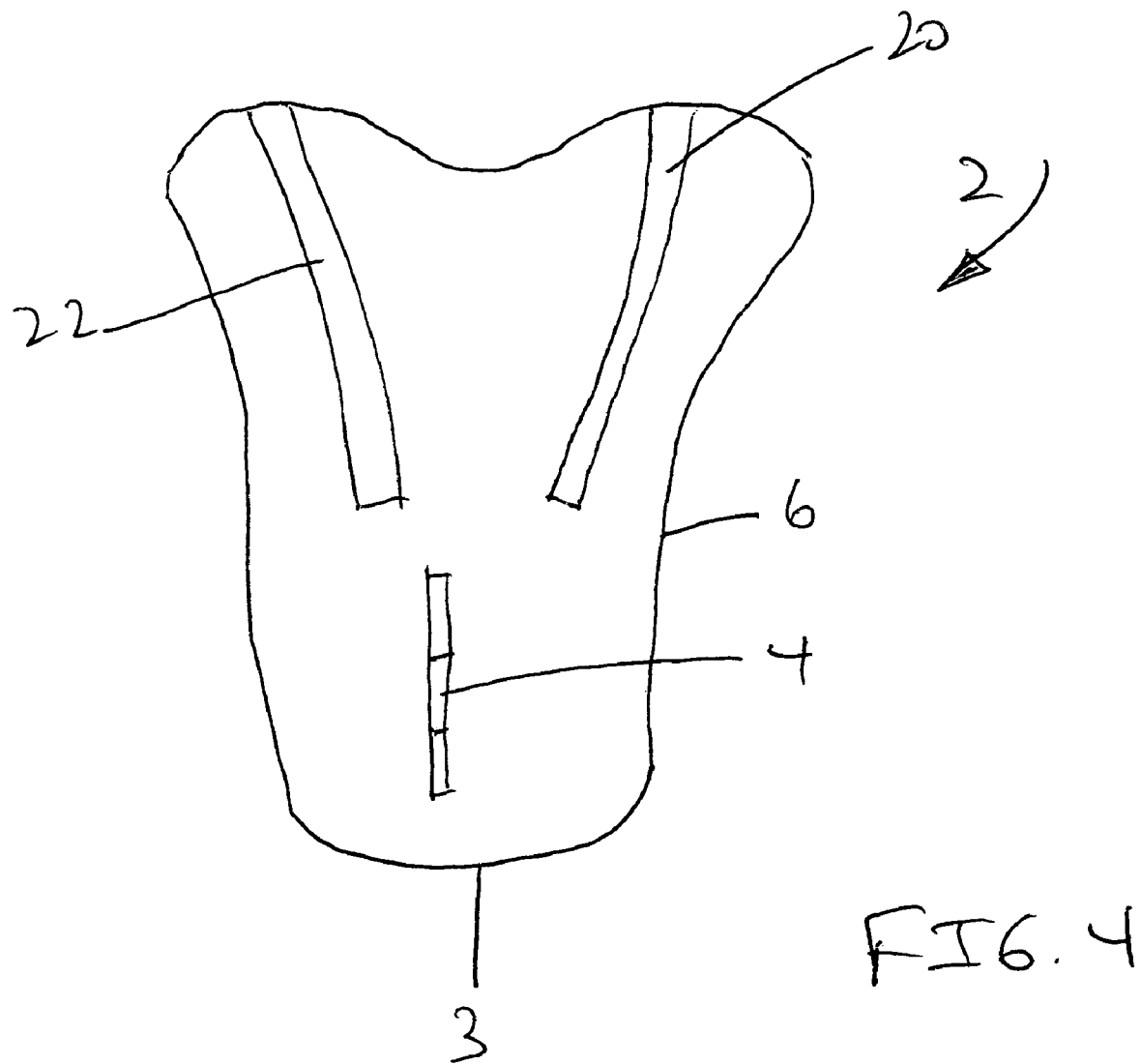
FIG. 4 shows a perspective view of the present invention with the tunnels in the nostril piece.

FIG. 3 shows a representative view of the inhaler 2 as it would appear in use.

The invention claimed is:

1. An apparatus for providing oxygen to an individual, the apparatus comprising:
   (a) an outer casing having a top end and a bottom end, the bottom end being open,
   (b) an oxygen canister having a top end and a bottom end, the top end of the oxygen canister having a pressure valve,
   (c) a volume of pressurized oxygen located within the oxygen canister,
   (d) a slide lever dispenser attached to the top end of the outer casing,
   (e) a nostril piece having a first end and a second end, the first end of the nostril piece attached to the top end of the outer casing,
   (f) a first tunnel and a second tunnel, each tunnel located within the nostril piece, each tunnel having a first end and a second end, the first end of each tunnel located at the first end of the nostril piece, the second end of each tunnel located at the second end of the nostril piece, the first tunnel and the second tunnel being separate and fluidly non-connecting,
   (g) wherein the oxygen canister is inserted through the bottom end of the outer casing such that the pressure valve of the oxygen canister rests against the slide lever dispenser,
   (h) further wherein engagement of the slide lever dispenser causes a small amount of oxygen within the oxygen canister to be released through the pressure valve directly into the nostril piece.

2. An apparatus for providing oxygen to an individual according to claim 1 wherein the nostril piece is cushioned.

3. An apparatus for providing oxygen to an individual according to claim 1 wherein the amount of oxygen within the oxygen canister that is released through the pressure valve travels through the pair of tunnels and exits the second end of each tunnel, further wherein the oxygen is available for medical use.

4. An apparatus for providing oxygen to an individual according to claim 3 wherein the oxygen that exits the second end of each tunnel is inhaled.

* * * * *